United States Patent
Burckhardt et al.

(10) Patent No.: US 9,212,287 B2
(45) Date of Patent: Dec. 15, 2015

(54) LOW-EMISSION HARDENER FOR EPOXY RESINS

(75) Inventors: Urs Burckhardt, Zurich (CH); Andreas Kramer, Zurich (CH); Ursula Stadelmann, Zurich (CH); Edis Kasemi, Zurich (CH)

(73) Assignee: SIKA TECHNOLOGY AG, Baar (CH)

( * ) Notice: Subject to any disclaimer, the term of this patent is extended or adjusted under 35 U.S.C. 154(b) by 71 days.

(21) Appl. No.: 14/125,672

(22) PCT Filed: Jul. 9, 2012

(86) PCT No.: PCT/EP2012/063378
§ 371 (c)(1),
(2), (4) Date: Dec. 12, 2013

(87) PCT Pub. No.: WO2013/010842
PCT Pub. Date: Jan. 24, 2013

(65) Prior Publication Data
US 2014/0107313 A1 Apr. 17, 2014

(30) Foreign Application Priority Data
Jul. 15, 2011 (EP) .................................... 11174275

(51) Int. Cl.
*C07C 211/27* (2006.01)
*C08G 59/50* (2006.01)
*C08G 59/56* (2006.01)
*C09D 163/00* (2006.01)
*C09K 3/00* (2006.01)
*C09D 7/12* (2006.01)
*C08L 63/00* (2006.01)

(52) U.S. Cl.
CPC ............ *C09D 7/1233* (2013.01); *C07C 211/27* (2013.01); *C08G 59/50* (2013.01); *C08G 59/5033* (2013.01); *C08G 59/56* (2013.01); *C08L 63/00* (2013.01); *C09D 163/00* (2013.01); *C09K 3/00* (2013.01)

(58) Field of Classification Search
None
See application file for complete search history.

(56) References Cited

U.S. PATENT DOCUMENTS

| | | | | |
|---|---|---|---|---|
| 3,597,149 | A | * | 8/1971 | Masuda et al. ................. 8/602 |
| 3,634,316 | A | * | 1/1972 | Ito et al. ........................ 524/255 |
| 3,947,389 | A | * | 3/1976 | Ito et al. ........................ 521/128 |
| 6,562,934 | B2 | | 5/2003 | Yonehama et al. |
| 2009/0163676 | A1 | | 6/2009 | Vedage et al. |
| 2011/0069846 | A1 | | 3/2011 | Cheng et al. |
| 2011/0082248 | A1 | | 4/2011 | Butikofer |

FOREIGN PATENT DOCUMENTS

| | | |
|---|---|---|
| EP | 1 188 740 A2 | 3/2002 |
| EP | 1 437 393 A1 | 7/2004 |
| EP | 2 133 378 A1 | 12/2009 |
| EP | 2 336 213 A1 | 6/2011 |

OTHER PUBLICATIONS

HCAPLUS accession No. 1948:5710 for the Helvetica Chimica Acta article by Ruggli et al., "Heterocyclic nitrogen compounds. LIX. Derivatives of m-xylylenediamine," vol. 30, 1947, with registry No. 25790-40-3, three pages.*
HCAPLUS accession No. 1975:44413 for Japanese Patent No. 49-17418 B, Ito et al., Apr. 30, 1974, one page.*
HCAPLUS accession No. 1978:132017 for Japanese Patent No. 52-45773 B, Satomi et al., Nov. 18, 1977, one page.*
Rugglie et al., "Ueber Derivate von m-Xylylen-diamin," *Helvetica Chimica Acta*, Jan. 1947, vol. 30, pp. 1845-1850. (XP009006309; ISSN: 0018-019X).
International Search Report issued in International Patent Application No. PCT/EP2012/063378 dated Aug. 8, 2012.
International Preliminary Report on Patentability issued in International Patent Application No. PCT/EP2012/063378 dated Jan. 21, 2014.

* cited by examiner

*Primary Examiner* — Robert Sellers
(74) *Attorney, Agent, or Firm* — Oliff PLC

(57) ABSTRACT

The present invention concerns a low-odor, low-viscosity hardener for epoxy resins comprising the amine of formula (I),

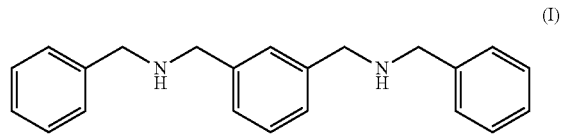

(I)

as well as a method for thinning of hardeners for epoxy resins by adding the amine of formula (I). These hardeners harden with epoxy resins quickly and without blushing to form films of high hardness and little brittleness, even without non-incorporable thinners such as benzyl alcohol. They are especially suitable for low-emission coatings.

17 Claims, No Drawings

LOW-EMISSION HARDENER FOR EPOXY RESINS

TECHNICAL FIELD

The invention concerns the field of amines and their use as hardeners for epoxy resins, as well as amine-containing epoxy resin compositions and their use, especially as a coating.

PRIOR ART

Epoxy resin compositions should have a number of properties in order to be useful as a high-quality coating. On the one hand, they should have a low viscosity, so that they are readily workable and self-running at ambient temperature, and they should harden quickly without any so-called blushing effects, even under damp cold conditions. By "blushing" is meant defects upon hardening such as turbidity, spots, and rough or sticky surface, typically caused by salt formation of amines with carbon dioxide ($CO_2$) in the air, with high humidity and low temperatures favoring the blushing effects. In the hardened state, the epoxy resin coating should have an even surface with no turbidity, spots or craters, and it should possess a good hardness with the least possible brittleness, in order to withstand mechanical stress, which is especially important when used as a protective coating or a floor covering. To achieve these properties, thinners are normally used in epoxy resin coatings of the prior art. Such thinners, like benzyl alcohol or phenols, greatly improve the workability and reduce the brittleness, but they are not incorporated into the resin matrix upon hardening. Yet the demand for low-emission systems that have a low content of substances which can be released by evaporation or diffusion processes after hardening is becoming increasingly important today. Therefore, thinners which cannot be incorporated can only be used in very slight amount or not at all in low-emission systems. Another possibility of thinning epoxy resin compositions is the adding of low-molecular amines, such as isophorone diamine, xylylene diamine or dimethylaminopropylamine. But such low-molecular amines usually have a strong odor and are very irritating to the skin, and they lead to blushing effects under damp, cold conditions.

US 2009/0163676 specifies hardeners for epoxy resins containing at least one benzylated polyalkylene polyamine and at least one additional amine. U.S. Pat. No. 6,562,934 specifies hardeners for epoxy resins containing reaction products of diamines with alkenyl compounds. The hardeners of these two documents have the drawback that they harden slowly with epoxy resins, especially at low temperatures, and without the use of non-incorporable thinners they result in rather brittle coatings.

PRESENTATION OF THE INVENTION

The problem of the present invention is therefore to provide hardeners for epoxy resins that are low-odor, low-viscosity, and readily workable with epoxy resins, and which harden even under damp, cold conditions quickly and without blushing, even without the presence of non-incorporable thinners.

Surprisingly, it has been discovered that hardeners according to claim 1 comprising the amine of formula (I) solve these problems. The hardener is low-odor, low-viscosity, and outstandingly compatible with epoxy resins. It hardens with them even under damp, cold conditions quickly and forms films that are not sticky, have a high luster, are free of turbidity and surface defects, and possess surprisingly high hardness.

Since the amine of formula (I) has no primary but rather only two secondary amino groups and a comparatively high NE equivalent weight, the person skilled in the art would expect slowly hardening, sticky and/or not very hard films.

With the hardener of claim 1, low-emission epoxy resin systems are accessible that fulfill the conditions for the Eco Seal of Approval, such as Emicode (EC1 Plus), AgBB, DIBt, Der Blaue Engel, AFSSET, RTS (M1) and US Green Building Council (LEED), and at the same time satisfy high demands with regard to processing and service properties, which is not possible with hardeners of the prior art.

Further aspects of the invention are the subject matter of further independent claims. Especially preferred embodiments of the invention are the subject matter of the dependent claims.

WAYS OF IMPLEMENTING THE INVENTION

The subject matter of the invention is a hardener suitable for the hardening of epoxy resins, comprising the amine of formula (I).

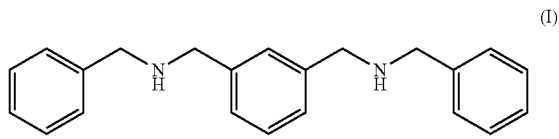 [SMILES: c1ccc(CNCc2cccc(CNCc3ccccc3)c2)cc1]

(I)

Substance terms starting with "poly", such as polyamine, polyol or polyepoxide, designate substances that formally contain two or more of the functional groups appearing in their name in each molecule.

By "aliphatic" is meant an amine whose amino group is bound to an aliphatic, cycloaliphatic or arylaliphatic residue; accordingly, this group is termed an aliphatic amino group.

By "aromatic" is meant an amine whose amino group is bound to an aromatic residue; accordingly, this group is termed an aromatic amino group.

By "amine hydrogen" is meant the hydrogen atoms of primary and secondary amino groups.

By "NH equivalent weight" is meant the weight fraction of a hardener or an amine per amine hydrogen present in the hardener or in the amine.

By "non-incorporable thinner" is meant a substance that is soluble in an epoxy resin and that lowers its viscosity, which is not covalently incorporated into the resin matrix upon the hardening of the epoxy resin.

By "viscosity" is meant in the present document the dynamic viscosity or shear viscosity, which is defined by the ratio between the shear stress and the shear rate (velocity gradient) and determined as described in DIN EN ISO 3219.

The amine of formula (I) can be obtained especially advantageously by the reductive alkylation of 1,3-bis-(aminomethyl)benzene (=meta-xylylene diamine or MXDA) with benzaldehyde. The benzaldehyde is used preferably stoichiometrically in relation to the primary amino groups of 1,3-bis-(aminomethyl)benzene. The reductive alkylation is carried out preferably in presence of hydrogen and under elevated pressure. It can occur directly with molecular hydrogen or indirectly by hydrogen transfer from other reagents. Molecular hydrogen is used preferably. The conditions are advantageously chosen such that, on the one hand, the primary amino groups are reductively alkylated as completely as possible and, on the other hand, the benzene rings are not hydrogenated. One works preferably at a hydrogen pressure of 5 to 100 bar, a temperature of 40 to 120° C., and in presence of a suitable catalyst. Preferable as the catalyst are palladium on carbon (Pd/C), platinum on carbon (Pt/C), Adams catalyst and Raney nickel, especially palladium on carbon and platinum on carbon.

The production of the amine of formula (I) by reductive alkylation in the described manner is especially advantageous for the use as a component of hardeners for epoxy resins, since primary amino groups are alkylated very selectively, while secondary amino groups are hardly alkylated any further. The product of the described preparation can therefore be used after the reductive alkylation with no further processing for the hardening of epoxy resins in the described manner.

The amine of formula (I) can also be obtained in ways other than reductive alkylation, especially by reaction of 1,3-bis-(aminomethyl)benzene with benzyl chloride or benzyl bromide in a suitable ratio. This produces reaction mixtures which typically have a substantial fraction of double alkylated amino groups.

The amine of formula (I) is a slightly volatile, low-odor substance of low viscosity. It has so little reactivity with respect to $CO_2$ that it has no tendency in air either to form a crust or to precipitation or increased viscosity—unlike many amines of the prior art. It shows an excellent compatibility with other amines and with epoxy resins.

Hardeners comprising the amine of formula (I) have a low viscosity with a relatively high NH-equivalent weight and thus are good thinners for epoxy resins. They harden surprisingly fast with epoxy resins and with no blushing effects, especially also at low temperatures. When applied in a coat, one gets regular, non-tacky films of surprisingly high hardness.

The hardener according to the invention, suitable for the hardening of epoxy resins, besides the amine of formula (I) also additionally contains in particular at least one polyamine A, which has at least three amine hydrogens that are reactive with respect to epoxy groups.

Hardeners comprising the amine of formula (I) in combination with a polyamine A additionally lead to an acceleration of the hardening of epoxy resins, resulting in hardened resins which have a higher hardness with little brittleness. This is especially advantageous for applications as a coating. Hardeners comprising the amine of formula (I) in combination with a polyamine A likewise have a low viscosity. In particular, the viscosity of the hardener is also low when the polyamine A has a much higher viscosity than the amine of formula (I). The amine of formula (I) thus acts to substantially thin the polyamine A, especially when the latter is more viscous. The amine of formula (I) thus allows us to effectively thin a polyamine A without using a non-incorporable thinner or a strong-odor amine with a tendency to blushing effects. The thinning is especially advantageous for polyamine A with a viscosity above 700 mPa·s, especially above 1500 mPa·s. Thanks to the presence of the amine of formula (I), the rate of hardening of the hardener with epoxy resins and the hardness and surface quality of such films is surprisingly not negatively affected and the brittleness is additionally reduced.

The following polyamines are especially suitable as the polyamine A:

aliphatic, cycloaliphatic or arylaliphatic primary diamines, such as ethylene diamine, 1,2-propane diamine, 1,3-propane diamine, 2-methyl-1,2-propane diamine, 2,2-dimethyl-1,3-propane diamine, 1,3-butane diamine, 1,4-butane diamine, 1,3-pentane diamine (DAMP), 1,5-pentane diamine, 1,5-diamino-2-methylpentane (MPMD), 2-butyl-2-ethyl-1,5-pentane diamine (C11-Neodiamine), 1,6-hexane diamine, 2,5-dimethyl-1,6-hexane diamine, 2,2,4- and 2,4,4-trimethylhexamethylene diamine (TMD), 1,7-heptane diamine, 1,8-octane diamine, 1,9-nonane diamine, 1,10-decane diamine, 1,11-undecane diamine, 1,12-dodecane diamine, 1,2-, 1,3- and 1,4-diaminocyclohexane, bis-(4-aminocyclohexyl)methane ($H_{12}$-MDA), bis-(4-amino-3-methylcyclohexyl)methane, bis-(4-amino-3-ethylcyclohexyl)methane, bis-(4-amino-3,5-dimethylcyclohexyl)methane, bis-(4-amino-3-ethyl-5-methylcyclohexyl)methane (M-MECA), 1-amino-3-aminomethyl-3,5,5-trimethylcyclohexane (=isophorone diamine or IPDA), 2- and 4-methyl-1,3-diaminocyclohexane and mixtures thereof, 1,3- and 1,4-bis-(amino-methyl)cyclohexane, 2,5(2,6)-bis-(aminomethyl)bicyclo[2.2.1]heptane (NBDA), 3(4), 8(9)-bis-(aminomethyl)tricyclo[5.2.1.0$^{2,6}$]decane, 1,4-diamino-2,2,6-trimethylcyclohexane (TMCDA), 1,8-menthane diamine, 3,9-bis-(3-aminopropyl)-2,4,8,10-tetraoxaspiro[5.5]undecane as well as 1,3- and 1,4-bis-(aminomethyl)benzene;

aliphatic, cycloaliphatic or arylaliphatic primary triamines like 4-aminomethyl-1,8-octane diamine, 1,3,5-tris-(aminomethyl)benzene, 1,3,5-tris-(aminomethyl)cyclohexane, tris-(2-aminoethyl)amine, tris-(2-aminopropyl)amine and tris-(3-aminopropyl)amine;

aliphatic primary diamines containing ether groups, such as especially bis-(2-aminoethyl)-ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine and higher oligomers of these diamines, bis-(3-aminopropyl)polytetrahydrofurans and other polytetrahydrofuran diamines, as well as polyoxyalkylene diamines. The latter typically constitute products from the amination of polyoxyalkylene diols and are available for example under the names Jeffamine® (from Huntsman), under the name Polyetheramine (from BASF) or under the name PC Amine® (from Nitroil). Especially suitable polyoxyalkylene diamines are Jeffamine® D-230, Jeffamine® D-400, Jeffamine® D-2000, Jeffamine® D-4000, Jeffamine® XTJ-511, Jeffamine® ED-600, Jeffamine® ED-900, Jeffamine ED-2003, Jeffamine® XTJ-568, Jeffamine® XTJ-569, Jeffamine® XTJ-523, Jeffamine® XTJ-536, Jeffamine® XTJ-542, Jeffamine® XTJ-559, Jeffamine® EDR-104, Jeffamine® EDR-148, Jeffamine® EDR-176; Polyetheramine D 230, Polyetheramine D 400 and Polyetheramine D 2000, PC Amine® DA 250, PC Amine® DA 400, PC Amine® DA 650 and PC Amine® DA 2000;

primary polyoxyalkylene triamines, which typically constitute products from the amination of polyoxyalkylene triols and are available for example under the name Jeffamine® (from Huntsman), under the name polyetheramine (from BASF) or under the name PC Amine® (from Nitroil), such as in particular Jeffamine® T-403, Jeffamine T-3000, Jeffamine® T-5000, Polyetheramine T 403, Polyetheramine T 5000 and PC Amine® TA 403;

polyamines having tertiary amino groups with two primary aliphatic amino groups, such as in particular N,N'-bis-(aminopropyl)-piperazine, N,N-bis-(3-aminopropyl)methylamine, N,N-bis-(3-aminopropyl)ethylamine, N,N-bis-(3-aminopropyl)propylamine, N,N-bis-(3-aminopropyl)cyclohexylamine, N,N-bis-(3-aminopropyl)-2-ethyl-hexylamine, as well as the products from the double cyanoethylation and subsequent reduction of fatty amines, which are derived from natural fatty acids, such as N,N-bis-(3-aminopropyl)dodecylamine and N,N-bis-(3-aminopropyl) tallow-alkylamine, available as Triameen® Y12D and Triameen® YT (from Akzo Nobel);

polyamines having tertiary amino groups with three primary aliphatic amino groups, such as in particular tris-(2-aminoethyl)amine, tris-(2-aminopropyl)amine and tris-(3-aminopropyl)amine;

polyamines having secondary amino groups with two primary aliphatic amino groups, such as in particular 3-(2-aminoethyl)aminopropylamine, bis-hexamethylene triamine (BHMT), diethylene triamine (DETA), triethylene tetramine (TETA), tetraethylene pentamine (TEPA), pentaethylene hexamine (PEHA) and higher homologues of linear polyethylene amines like polyethylene polyamine with 5 to 7 ethylene amine units (so-called "higher ethylene-polyamines", HEPA), products from the multiple cyanoethylation or cyanobutylation and subsequent hydrogenation of primary di- and polyamines with at least two primary amino groups, such as dipropylene triamine (DPTA), N-(2-aminoethyl)-1,3-propane diamine (N3-amine), N,N'-bis(3-aminopropyl)ethylene diamine (N4-amine), N,N'-bis-(3-aminopropyl)-1,4-diaminobutane, N5-(3-aminopropyl)-2-methyl-1,5-pentane diamine, N3-(3-aminopentyl)-1,3-pentane diamine, N5-(3-amino-1-ethylpropyl)-2-methyl-1,5-pentane diamine and N,N'-bis-(3-amino-1-ethylpropyl)-2-methyl-1,5-pentane diamine.

polyamines having one primary and one secondary amino group, such as in particular N-methyl-1,2-ethane diamine, N-ethyl-1,2-ethane diamine, N-butyl-1,2-ethane diamine, N-hexyl-1,2-ethane diamine, N-(2-ethylhexyl)-1,2-ethane diamine, N-cyclohexyl-1,2-ethane diamine, 4-aminomethyl-piperidine, N-(2-aminoethyl)piperazine, N-methyl-1,3-propane diamine, N-butyl-1,3-propane diamine, N-(2-ethylhexyl)-1,3-propane diamine, N-cyclohexyl-1,3-propane diamine, 3-methylamino-1-pentylamine, 3-ethylamino-1-pentylamine, 3-cyclohexylamino-1-pentylamine, fatty diamines like N-cocoalkyl-1,3-propane diamine and products from the Michael-type addition reaction of primary aliphatic diamines with acrylonitrile, maleic or fumaric acid diesters, citraconic acid diesters, acrylic and methacrylic acid esters, acrylic and methacrylic acid amides and itaconic acid diesters, reacted in a molar ratio of 1:1, and also products from the partial reductive alkylation of primary aliphatic polyamines with benzaldehyde or other aldehydes or ketones, as well as partially styrolized polyamines like Gaskamine® 240 (from Mitsubishi Gas Chemical (MGC));

aromatic polyamines, especially such as m- and p-phenylene diamine, 4,4'-, 2,4' and 2,2'-diaminodiphenylmethane, 3,3'-dichloro-4,4'-diaminodiphenylmethane (MOCA), 2,4- and 2,6-toluylene diamine, mixtures of 3,5-dimethylthio-2,4- and -2,6-toluylene diamine (available as Ethacure® 300 from Albemarle), mixtures of 3,5-diethyl-2,4- and -2,6-toluylene diamine (DETDA), 3,3',5,5'-tetraethyl-4,4'-diaminodiphenylmethane (M-DEA), 3,3',5,5'-tetraethyl-2,2'-dichloro-4,4'-diaminodiphenylmethane (M-CDEA), 3,3'-diisopropyl-5,5'-dimethyl-4,4'-diaminodiphenylmethane (M-MIPA), 3,3',5,5'-tetraisopropyl-4,4'-diaminodiphenylmethane (M-DIPA), 4,4'-diaminodiphenylsulfone (DDS), 4-amino-N-(4-aminophenyl)benzene sulfonamide, 5,5'-methylene dianthranilic acid, dimethyl-(5,5'-methylene dianthranilate), 1,3-propylene-bis-(4-aminobenzoate), 1,4-butylene-bis-(4-aminobenzoate), polytetramethylene oxide-bis-(4-aminobenzoate) (available as Versalink® from Air Products), 1,2-bis-(2-aminophenylthio)ethane, 2-methylpropyl-(4-chloro-3,5-diaminobenzoate) and tert.butyl-(4-chloro-3,5-diaminobenzoate);

adducts of the mentioned polyamines with epoxides and epoxy resins, especially adducts with diepoxides in a molar ratio of at least 2/1, adducts with monoepoxides in a molar ratio of at least 1/1, and reaction products from amines and epichlorhydrin, especially that of 1,3-bis-(aminomethyl)benzene, commercially available as Gaskamine® 328 (from MGC);

polyamidoamines, which constitute reaction products of a monovalent or polyvalent carboxylic acid, or its esters or anhydrides, especially a dimer fatty acid, and an aliphatic, cycloaliphatic or aromatic polyamine used in stoichiometric excess, especially a polyalkylene amine such as DETA or TETA, especially the commercially available polyamidoamines Versamid® 100, 125, 140 and 150 (from Cognis), Aradur® 223, 250 and 848 (from Huntsman), Euretek® 3607 and 530 (from Huntsman) and Beckopox® EH 651, EH 654, EH 655, EH 661 and EH 663 (from Cytec); and phenalkamines, also known as Mannich bases, which constitute reaction products of a Mannich reaction of phenols, especially cardanol, with aldehydes, especially formaldehyde, and polyamines, especially the commercially available phenalkamines Cardolite® NC-541, NC-557, NC-558, NC-566, Lite 2001 and Lite 2002 (from Cardolite), Aradur® 3440, 3441, 3442 and 3460 (from Huntsman) and Beckopox® EH 614, EH 621, EH 624, EH 628 and EH 629 (from Cytec).

Chosen preferably as polyamine A are polyamines from the group consisting of 1,3-pentane diamine (DAMP), 1,5-diamino-2-methylpentane (MPMD), 2-butyl-2-ethyl-1,5-pentane diamine (C11-Neodiamine), 1,6-hexane diamine, 2,2,4- and 2,4,4-trimethylhexamethylene diamine (TMD), 1,12-dodecane diamine, 1,3-diaminocyclohexane, bis-(4-aminocyclohexyl)methane ($H_{12}$-MDA), bis-(4-amino-3-methylcyclohexyl)methane, 1-amino-3-aminomethyl-3,5,5-trimethylcyclohexane (IPDA), 1,3-bis-(aminomethyl)cyclohexane, 1,3-bis-(amino-methyl)benzenel (MXDA), bis-hexamethylene triamine (BHMT), diethylene triamine (DETA), triethylene tetramine (TETA), tetraethylene pentamine (TEPA), pentaethylene hexamine (PEHA) and higher homologues of linear polyethylene amines like polyethylene polyamines with 5 to 7 ethylene amine units (HEPA), dipropylene triamine (DPTA), N-(2-aminoethyl)-1,3-propane diamine (N3-amine), N,N'-bis(3-aminopropyl)ethylene diamine (N4-amine), polyoxyalkylene diamines and polyoxyalkylene triamines with a molecular weight in the range of 200 to 500 g/mol, especially the types Jeffamine® D-230, Jeffamine® D-400 and Jeffamine® T-403, polyamidoamines, phenalkamines, compounds of the mentioned polyamines that are partially or fully alkylated to primary amino groups and adducts of the mentioned polyamines with epoxides and epoxy resins.

These preferred polyamines A are especially compatible with epoxy resins and produce films of very good quality.

Especially preferred as the polyamine A are polyamines having at least one secondary amino group, especially phenalkamines, adducts of polyamines with epoxides and epoxy resins, as well as primary polyamines which are alkylated to at least one primary amino group, especially styrolized 1,3-bis-(aminomethyl)benzene and benzylated polyalkylene amines. These preferred polyamines A have little tendency to blushing effects and yield films of especially high quality with epoxy resins, even under damp, cold conditions. But many of these amines have a high viscosity, so that without thinning they only have an inadequate workability as an epoxy resin coating. For low-emission coatings, their combination with the amine of formula (I) is especially advantageous, since this makes possible low-viscosity hardeners that have little tendency to blushing and that harden into films of high hardness with little brittleness, even without the presence of non-incorporable thinners.

Also especially suitable as the polyamine A are mixtures comprising several of the mentioned polyamines.

Most preferred as the polyamine A are polyamines which in themselves have good properties as a coating with epoxy resins, but which have a high viscosity and which for reasons of workability and/or too high brittleness would certainly be combined with non-incorporable thinners, such as benzyl alcohol, alkyl phenols, styrolized phenol or hydrocarbon resins, in order to meet the requirements for high-quality coatings. But the compositions with such non-incorporable thinners are not suitable for applications where low-emission systems are demanded. However, thanks to the amine of formula (I), which is fully incorporated into the resin matrix upon hardening, no emissions occur after the hardening.

If the hardener contains, besides the amine of formula (I), also a polyamine A, then the ratio of the number of amine hydrogens of the amine of formula (I) that are reactive to epoxy groups and the number of amine hydrogens of the polyamine A that are reactive to epoxy groups is typically in the range of 0.05:1 to 5:1, especially 0.05:1 to 2:1. Such hardeners have a reduced viscosity and harden with epoxy resins into films of little brittleness and a broadly adjustable hardness, from moderate when larger amounts of the amine of formula (I) are used to high when a lesser amount of the amine of formula (I) is used. Especially preferably this ratio lies in the range of 0.1:1 to 1:1. Such hardeners are distinguished by a low viscosity and a rapid hardening with epoxy resins to form films of high hardness and little brittleness.

In the described hardener, the weight ratio of the amine of formula (I) and the polyamine A lies preferably in the range of 0.2:1 to 2:1, especially in the range of 0.4:1 to 1.5:1. Such hardeners are distinguished by a low viscosity and a fast hardening with epoxy resins to form.

The hardener according to the invention can also comprise at least one accelerator in addition to the amine of formula (I).

Suitable as the accelerator are substances which accelerate the reaction between amino groups and epoxy groups, especially acids or compounds which can be hydrolyzed to acids, especially organic carboxylic acids like acetic acid, benzoic acid, salicylic acid, 2-nitrobenzoic acid, lactic acid, organic sulfonic acids like methane sulfonic acid, p-toluene sulfonic acid or 4-dodecylbenzene sulfonic acid, sulfonic acid esters, other organic or inorganic acids like in particular phosphoric acid, or mixtures of the aforementioned acids and acid esters; furthermore tertiary amines like in particular 1,4-diazabicyclo[2.2.2]octane, benzyldimethylamine, α-methyl-benzyldimethylamine, triethanol amine, dimethyl-aminopropylamine, imidazoles like in particular N-methylimidazole, N-vinylimidazole or 1,2-dimethylimidazole, salts of such tertiary amines, quaternary ammonium salts, like in particular benzyltrimethylammonium chloride, amidines like in particular 1,8-diazabicyclo[5.4.0]undec-7-ene, guanidines like in particular 1,1,3,3-tetramethylguanidine, phenols, especially bisphenols, phenol resins and Mannich bases like in particular 2-(dimethylaminomethyl)phenol, 2,4,6-tris-(dimethylaminomethyl)phenol and polymers of phenol, formaldehyde and N,N-dimethyl-1,3-propane diamine, phosphites like in particular di- and triphenyl phosphites, as well as compounds having mercapto groups, such as have already been mentioned above.

Preferred accelerators are salicylic acid and 2,4,6-tris-(dimethylaminomethyl)phenol.

The hardener according to the invention can furthermore comprise, in addition to the amine of formula (I), at least onenon-incorporablethinner, such as in particular xylene, 2-methoxyethanol, dimethoxyethanol, 2-ethoxyethanol, 2-propoxyethanol, 2-isopropoxyethanol, 2-butoxyethanol, 2-phenoxyethanol, 2-benzyloxyethanol, benzyl alcohol, ethylene glycol, ethylene glycol dimethyl ether, ethylene glycol diethyl ether, ethylene glycol dibutyl ether, ethylene glycol diphenyl ether, diethylene glycol, diethylene glycol monomethyl ether, diethylene glycol monoethyl ether, diethylene glycol mono-n-butyl ether, diethylene glycol dimethyl ether, diethylene glycol diethyl ether, diethylene glycol di-n-butylyl ether, propylene glycol butyl ether, propylene glycol phenyl ether, dipropylene glycol, dipropylene glycol monomethyl ether, dipropylene glycol dimethyl ether, dipropylene glycol di-n-butyl ether, N-methyl pyrrolidone, diphenyl methane, diisopropyl naphthaline, petroleum fractions such as Solvesso® types (from Exxon), alkyl phenols like tert.butyl phenol, nonyl phenol, dodecyl phenol and 8,11,14-pentadecatrienyl phenol (Cardanol, from cashew shell oil, available for example as Cardolite NC-700 from Cardolite Corp., USA), styrolized phenol, bisphenols, aromatic hydrocarbon resins, especially types containing phenol groups, adipates, sebacates, phthalates, benzoates, organic phosphoric and sulfonic acid esters and sulfonamides. Preferred are benzyl alcohol, dodecyl phenol, tert.butyl phenol, styrolized phenol and aromatic hydrocarbon resins containing phenol groups, especially Novares® types LS 500, LX 200, LA 300 and LA 700 (from Rütgers).

Preferably the hardener contains little or no content ofnon-incorporablethinners, especially preferably less than 25 wt. %, particularly less than 10 wt. %, and most preferably less than 5 wt. %. In particular, nonon-incorporablethinner is added to the hardener.

Furthermore, the described hardener can contain other substances reactive to epoxy groups, such as in particular monoamines, like in particular benzylamine, cyclohexylamine, 2-phenylethylamine, 2-methoxyphenylethylamine, 4-methoxyphenylethylamine, 3,4-dimethoxyphenylethylamine (homoveratryl amine), 1- and 2-butylamine, isobutylamine, tert.-butylamine, 3-methyl-2-butylamine, 1-hexylamine, 1-octylamine, 2-ethyl-1-hexylamine, 2-methoxy-1-ethylamine, 2-ethoxy-1-ethylamine, 3-methoxy-1-propylamine, 3-ethoxy-1-propylamine, 3-(2-ethylhexyloxy)propylamine, 3-(2-methoxyethoxy)propylamine;

secondary aliphatic polyamines, such as in particular N,N'-dibutyl-ethylene diamine, N,N'-di-tert.butyl-ethylene diamine, N,N'-diethyl-1,6-hexane diamine, 1-(1-methylethyl-amino)-3-(1-methylethyl-aminomethyl)-3,5,5-trimethylcyclohexane (Jefflink® 754 from Huntsman), $N^4$-cyclohexyl-2-methyl-$N^2$-(2-methylpropyl)-2,4-pentane diamine, N,N'-dialkyl-1,3-xylylene diamine, bis-(4-(N-3-butylamino)-cyclohexyl)-methane (Clearlink® 1000 from UOP), N-alkylated polyetheramines, such as the Jeffamine® types SD-231, SD-401, ST-404 and SD-2001 (from Huntsman), products from the Michael-type addition reaction of primary aliphatic polyamines with Michael acceptors like acrylonitrile, maleic acid diesters, fumaric acid diesters, citraconic acid diesters, acrylic acid esters, methacrylic acid esters, cinnamic acid esters, itaconic acid diesters, vinylphosphonic acid diesters, vinylsulfonic acid aryl esters, vinylsulfones, vinylnitriles, 1-nitroethylene or Knoevenagel condensation products such as those from malonic acid diesters and aldehydes like formaldehyde, acetaldehyde or benzaldehyde, and also products from the reductive alkylation of primary aliphatic polyamines with benzaldehyde or other aldehydes or ketones;

liquid mercaptan-terminated polysulfide polymers, known under the brand names Thiokol® (from Morton Thiokol; for example available from SPI Supplies, or from Toray Fine Chemicals), especially the types LP-3, LP-33, LP-980, LP-23, LP-55, LP-56, LP-12, LP-31, LP-32 and LP-2; as well as those known under the brand names Thioplast® (from Akzo Nobel), especially the types G 10, G 112, G 131, G 1, G 12, G 21, G 22, G 44 and G 4;

mercaptan-terminated polyoxyalkylene ethers, available for example by reaction of polyoxyalkylene di- and triols either with epichlorhydrin or with an alkylene oxide, followed by sodium hydrogen sulfide;

mercaptan-terminated compounds in the form of polyoxyalkylene derivatives, known under the brand names Capcure® (from Cognis), especially the types WR-8, LOF and 3-800;

polyesters of thiocarboxylic acids, such as pentaerythritol tetramercaptoacetate, trimethylol propane trimercaptoacetate, glycol dimercaptoacetate, pentaerythritol tetra-(3-mercaptopropionate), trimethylol propane tri-(3-mercaptopropionate) and glycol di-(3-mercaptopropionate), as well as the esterification products of polyoxyalkylene diols and triols, ethoxylated trimethylol propane and polyester diols with thiocarboxylic acids like thioglycolic acid and 2- or 3-mercaptopropionic acid; and other compounds having mercapto groups, such as in particular 2,4,6-trimercapto-1,3,5-triazine, 2,2'-(ethylene dioxy)-diethane thiol (triethylene glycol dimercaptan) and ethane dithiol.

Another subject matter of the invention is an epoxy resin composition containing
a) at least one epoxy resin, and
b) at least one hardener comprising the amine of formula (I), as described above.

As the epoxy resin, conventional technical epoxy resins are suitable. These are obtained in the known manner, for example, from the oxidation of the corresponding olefins or from the reaction of epichlorhydrin with the corresponding polyols, polyphenols or amines.

Especially suitable as the epoxy resin are so-called polyepoxide liquid resins, hereinafter called "liquid resin". These have a glass transition temperature which usually lies below 25° C., in contrast with so-called solid resins, which have a glass transition temperature above 25° C. and can be comminuted into powders which are pourable up to 25° C.

In one embodiment, the liquid resin is an aromatic polyepoxide. Suitable for this, for example, are liquid resins of formula (II),

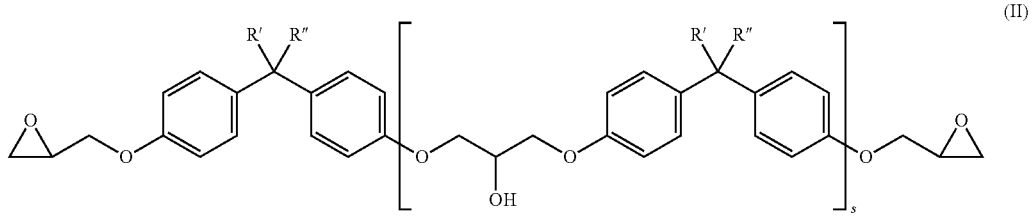

(II)

where R' and R" independently of one another each stand for a hydrogen atom or a methyl group, and s on average stands for a value of 0 to 1. Preferable are such liquid resins of formula (II) for which the index s on average stands for a value of less than 0.2.

The liquid resins of formula (II) are diglycidyl ethers of bisphenol-A, bisphenol-F and bisphenol-A/F, where A stands for acetone and F for formaldehyde, which serve as educts for the production of these bisphenols. A bisphenol-A liquid resin accordingly has methyl groups, a bisphenol-F liquid resin hydrogen atoms, and a bisphenol-A/F liquid resin both methyl groups and hydrogen atoms as R' and R" in formula (II). In the case of bisphenol-F, positional isomers can also be present, especially those derived from 2,4'- and 2,2'-hydroxyphenylmethane. Other suitable aromatic liquid resins are the glycidylization products of dihydroxybenzene derivatives such as resorcin, hydroquinone and pyrocatechol;

other bisphenols or polyphenols like bis-(4-hydroxy-3-methylphenyl)-methane, 2,2-bis-(4-hydroxy-3-methylphenyl)-propane (bisphenol-C), bis-(3,5-dimethyl-4-hydroxyphenyl)-methane, 2,2-bis-(3,5-dimethyl-4-hydroxyphenyl)-propane, 2,2-bis-(3,5-dibromo-4-hydroxyphenyl)-propane, 2,2-bis-(4-hydroxy-3-tert.-butylphenyl)-propane, 2,2-bis-(4-hydroxyphenyl)-butane (bisphenol-B), 3,3-bis-(4-hydroxyphenyl)-pentane, 3,4-bis-(4-hydroxyphenyl)-hexane, 4,4-bis-(4-hydroxyphenyl)-heptane, 2,4-bis-(4-hydroxyphenyl)-2-methylbutane, 2,4-bis-(3,5-dimethyl-4-hydroxyphenyl)-2-methylbutane, 1,1-bis-(4-hydroxyphenyl)-cyclohexane (bisphenol-Z), 1,1-bis-(4-hydroxyphenyl)-3,3,5-trimethylcyclohexane (bisphenol-TMC), 1,1-bis-(4-hydroxyphenyl)-1-phenylethane, 1,4-bis[2-(4-hydroxyphenyl)-2-propyl]-benzene) (bisphenol-P), 1,3-bis-[2-(4-hydroxyphenyl)-2-propyl]-benzene) (bisphenol-M), 4,4'-dihydroxydiphenyl (DOD), 4,4'-dihydroxybenzophenone, bis-(2-hydroxynaphth-1-yl)-methane, bis-(4-hydroxynaphth-1-yl)-methane 1,5-dihydroxy-naphthaline, tris-(4-hydroxyphenyl)-methane, 1,1,2,2-tetrakis-(4-hydroxyphenyl)-ethane, bis-(4-hydroxyphenyl)-ether, bis-(4-hydroxyphenyl) sulfone;

condensation products of phenols with formaldehyde, which are obtained under acidic conditions, such as phenol Novolaks or cresol Novolaks, also known as bisphenol-F Novolaks;

aromatic amines, like aniline, toluidine, 4-aminophenol, 4,4'-methylene diphenyldiamine (MDA), 4,4'-methylene diphenyldi-(N-methyl)-amine, 4,4'-[1,4-phenylenebis-(1-methyl-ethylidene)]-bisaniline (bisaniline-P), 4,4'-[1,3-phenylene-bis-(1-methyl-ethylidene)]-bisaniline (bisaniline-M).

Also suitable as the epoxy resin is an aliphatic or cycloaliphatic polyepoxide, such as a glycidyl ether of a saturated or unsaturated, branched or unbranched, cyclical or open-chain $C_2$- to $C_{30}$-diol, such as ethylene glycol, propylene glycol, butylene glycol, hexane diol, octane diol, a polypropylene glycol, dimethylol cyclohexane, neopentylglycol or dibromo-neopentylglycol;

a glycidyl ether of a tri- or tetrafunctional, saturated or unsaturated, branched or unbranched, cyclical or open-chain polyol, such as ricin oil, trimethylol propane, trimethylol ethane, pentaerythrol, sorbitol or glycerine, as well as alkoxylated glycerine or alkoxylated trimethylol propane;

a hydrogenatec bisphenol-A, -F or -A/F liquid resin, or the glycidylization products of hydrogenated bisphenol-A, -F or -A/F;

a N-glycidyl derivative of amides or heterocyclical nitrogen bases, such as triglycidyl cyanurate and triglycidyl isocyanurate, as well as reaction products of epichlorhydrin and hydantoin.

Also possible as the epoxy resin are a bisphenol-A, -F or -A/F solid resin, which is of similar structure to the already mentioned liquid resins of formula (II), but having a value of 2 to 12 instead of the index s, and having a glass transition temperature above 25° C.

Finally, also suitable as the epoxy resin are epoxy resins from the oxidation of olefins, such as from the oxidation of vinylcyclohexene, dicyclopentadiene, cyclohexadiene, cyclododecadiene, cyclododecatriene, isoprene, 1,5-hexadiene, butadiene, polybutadiene or divinylbenzene.

Preferred as the epoxy resin are liquid resins based on a bisphenol, especially based on bisphenol-A, bisphenol-F or bisphenol-A/F, as are commercially available, for example, from Dow, Huntsman and Hexion. These liquid resins have a low viscosity for epoxy resins and good properties as coatings in the hardened state. They can optionally be present in combination with bisphenol A solid resin or bisphenol-F Novolak epoxy resin.

The epoxy resin can contain a reactive thinner, especially a reactive thinner having at least one epoxy group. Suitable as the reactive thinner are, for example, the glycidylether monovalent or polyvalent phenols and aliphatic or cycloaliphatic alcohols, such as in particular the already mentioned polyglycidyl ethers of di- or polyols, and also in particular phenylglycidyl ether, cresylglycidyl ether, p-n-butylphenylglycidyl ether, p-tert.butyl-phenylglycidyl ether, nonylphenylglycidyl ether, allylglycidyl ether, butylglycidyl ether, hexylglycidyl ether, 2-ethylhexylglycidyl ether, as well as glycidyl ether of natural alcohols, such as $C_8$- to $C_{10}$-alkylglycidyl ether or $C_{12}$- to $C_{14}$-alkylglycidyl ether. The adding of a reactive thinner to the epoxy resin brings about a reduction of the viscosity, and also—in the hardened state of the epoxy resin composition—a reduction of the glass transition temperature and the mechanical values.

Optionally the epoxy resin composition contains other components, especially adjuvants and additives normally used in epoxy resin compositions, such as the following:

solvents, thinners, film forming aids or extenders, such as the already mentioned non-incorporable thinners;

reactive thinners, especially reactive thinners having epoxy groups, such as have been previously mentioned, epoxidated soy oil or linseed oil, compounds having acetoacetate groups, especially acetoacetylated polyols, butyrolactone, carbonates, aldehydes, and also isocyanates and silicones having reactive groups;

polymers, such as polyamides, polysulfides, polyvinylformal (PVF), polyvinylbutyral (PVB), polyurethanes (PUR), polymers with carboxyl groups, polyamides, butadiene-acrylonitrile copolymers, styrene-acrylonitrile copolymers, butadiene-styrene copolymers, homo- or copolymers of unsaturated monomers, especially from the group comprising ethylene, propylene, butylene, isobutylene, isoprene, vinylacetate and alkyl (meth)acrylates, especially chlorosulfonated polyethylenes and fluorine-containing polymers, sulfonamide-modified melamines and purified Montan waxes;

inorganic and organic fillers, such as ground or precipitated calcium carbonates, which are optionally coated with fatty acids, especially stearates, barite (heavy spar), talcs, ground quartz, quartz sand, micaceous iron ore, dolomites, wollastonites, kaolins, mica (potassium aluminum silicate), molecular sieves, aluminum oxides, aluminum hydroxides, magnesium hydroxide, silicic acids, cements, gypsum, fly ash, soot, graphite, metal powder such as aluminum, copper, iron, zinc, silver or steel, PVC powder or hollow spheres;

fibers, especially glass fibers, carbon fibers, metal fibers, ceramic fibers or plastic fibers like polyimide fibers or polyethylene fibers;

pigments, such as titanium dioxide and iron oxides;

the aforementioned accelerators;

rheology modifiers, such as in particular thickening agents, for example, sheet silicates like bentonites, derivatives of ricin oil, hydrogenated ricin oil, polyamides, polyurethanes, urea compounds, pyrogenic silicic acids, cellulose ether and hydrophobically modified polyoxyethylenes;

adhesion promoters such as organoalkoxysilanes like aminosilanes, mercaptosilanes, epoxysilanes, vinylsilanes, (meth)acrylosilanes, isocyanatosilanes, carbamatosilanes, alkylsilanes, S-(alkylcarbonyl)-mercaptosilanes and aldiminosilanes, as well as oligomeric forms of these silanes, especially 3-glycidoxypropyltrimethoxysilane, 3-aminopropyltrimethoxysilane, N-(2-aminoethyl)-3-aminopropyl-trimethoxysilane, N-(2-aminoethyl)-N'-[3-(trimethoxysilyl)propyl]ethylene diamine, 3-mercaptopropyltrimethoxysilane, 3-isocyanatopropyltrimethoxysilane, 3-ureidopropyltrimethoxysilane, 3-chloropropyltrimethoxysilane, vinyltrimethoxysilane, or the corresponding organosilanes with ethoxy groups instead of the methoxy groups;

stabilizers to oxidation, heat, light and UV radiation;

flame retardants, especially compounds like aluminum hydroxide ($Al(OH)_3$; also known as ATH for "aluminum trihydrate"), magnesium hydroxide ($Mg(OH)_2$; also called MDH for "magnesium dihydrate"), ammonium sulfate ($(NH_4)_2SO_4$), boric acid ($B(OH)_3$), zinc borate, zinc phosphate, melamine borate and melamine cyanurate; phosphorus-containing compounds such as ammonium phosphate ($(NH_4)_3PO_4$), ammonium polyphosphate, melamine phosphate, melamine pyrophosphate, triphenylphosphate, diphenylcresylphosphate, tricresylphosphate, triethylphosphate, tris-(2-ethylhexyl) phosphate, trioctylphosphate, mono-, bis- and tris-(isopropylphenyl)phosphate, resorcinol-bis (diphenylphosphate), resorcinol-diphosphate oligomer, tetraphenyl-resorcinol-diphosphite, ethylene diamine diphosphate and bisphenol-A-bis(diphenylphosphate); halogen-containing compounds such as chloroalkylphosphates, especially tris-(chloroethyl)phosphate, tris-(chloropropyl)phosphate and tris-(dichloroisopropyl)phosphate, polybrominated diphenylether, especially decabromodiphenylether, polybrominated diphenyloxide, tris-[3-bromo-2,2-bis(bromomethyl)propyl] phosphate, tetrabromo-bisphenol-A, bis-(2,3-dibromopropyl ether) of bisphenol A, brominated epoxy resins, ethylene-bis(tetrabromophtalimide), ethylene-bis(dibromonorbornane dicarboximide), 1,2-bis-(tribromophenoxy)ethane, tris-(2,3-dibromopropyl)isocyanurate, tribromophenol, hexabromocyclododecane, bis-(hexachlorocyclopentadieno)cyclooctane and chloroparaffins; as well as combinations of a halogen-containing compound and antimony trioxide ($Sb_2O_3$) or antimony pentoxide ($Sb_2O_5$);

surfactants, such as in particular crosslinking agents, leveling agents, deaerating agents or defoamers;

biocides, such as algicides, fungicides or substances inhibiting fungal growth.

Preferably the epoxy resin composition contains further adjuvants and additives, especially crosslinking agents, leveling agents, defoamers, stabilizers, pigments and accelerators, especially salicylic acid or 2,4,6-tris-(dimethylaminomethyl)phenol.

Preferably the epoxy resin composition contains little or no content of non-incorporable thinners, especially preferably less than 10 wt. %, especially less than 5 wt. %, and most preferably less than 2 wt. 5.

In the epoxy resin composition the ratio of the number of groups reactive to epoxy groups and the number of epoxy groups lies in the range of 0.5:1 to 1.5:1, preferably 0.7:1 to 1.2:1. The amine hydrogens present in the epoxy resin composition and any other groups present that are reactive to epoxy groups react with the epoxy groups when their ring is opened (addition reaction). As a result of these reactions, the composition is polymerized and finally hardens. The person skilled in the art is aware that primary amino groups are difunctional to epoxy groups and thus a primary amino group counts as two groups that are reactive to epoxy groups.

In particular, the epoxy resin composition is a two-component composition consisting of
(i) a resin component containing at least one epoxy resin and
(ii) a hardener component containing the hardener comprising the amine of formula (I), as described above.

The components of the two-component composition are each kept in their own container. Other ingredients of the two-component epoxy resin composition can be present as an ingredient of the resin or the hardener component, while other ingredients that are reactive to epoxy groups are preferably an ingredient of the hardener component. A suitable container for the storage of the resin or the hardener component is in particular a drum, a hobbock, a bag, a bucket, a can, a cartridge or a tube. The components are storeable, that is, they can be kept for several months up to one year or longer before being used, without changing in their respective properties to a relevant degree for their use.

To use the two-component epoxy resin composition, the resin component and the hardener component are mixed together shortly before or during the application. The mix ratio between the two components is preferably chosen such that the groups of the hardener component that are reactive to epoxy groups stand in a suitable relation to the epoxy groups of the resin component, as described above. In parts by weight, the mix ratio between the resin component and the hardener component is normally in the range of 1:10 to 10:1.

The mixing of the two components is done by means of a suitable method; it can be done continuously or in batches. If the mixing occurs prior to the application, one must make sure that not too much time passes between the mixing of the components and the application, since this may lead to disturbances, such as a slower or incomplete buildup of adhesion to the substrate. The mixing is done in particular at ambient temperature, which typically lies in the range of around 5 to 50° C., preferably around 10 to 30° C.

With the mixing of the two components, the hardening begins by chemical reaction, as described above. The hardening occurs in particular at ambient temperature, which typically lies in the range of around 5 to 50° C., preferably around 10 to 30° C. It extends typically over several days to weeks, until it is largely completed under the given conditions. The duration depends on the temperature, the reactivity of the components and their stoichiometry, as well as the presence of accelerators, among other things.

Another subject matter of the invention is thus also a hardened composition obtained from the hardening of an epoxy resin composition, as described in the present document.

The application of the epoxy resin composition is done on at least one substrate, the following ones being especially suitable:

glass, glass ceramics, concrete, mortar, brick, tile, plaster and natural stone like granite or marble;

metals and alloys, like aluminum, iron, steel and nonferrous metals, as well as surface-treated metals and alloys, such as galvanized or chrome-plated metals;

leather, textiles, paper, wood, wood-based materials bound with resins, such as phenol, melamine or epoxy resins, resin-textile composites and other so-called polymer composites;

plastics, such as polyvinylchloride (hard and soft PVC), acrylonitrile-butadiene-styrene copolymers (ABS), polycarbonate (PC), polyamide (PA), polyester, poly(methylmethacrylate) (PMMA), polyester, epoxy resins, polyurethanes (PUR), polyoxymethylene (POM), polyolefins (PO), polyethylene (PE) or polypropylene (PP), ethylene/propylene copolymers (EPM) and ethylene/propylene/diene terpolymers (EPDM), wherein the plastics can be surface-treated preferably by means of plasma, corona or flame;

fiber-reinforced plastics, such as carbon fiber reinforced plastics (CFK), glass fiber reinforced plastics (GFK) and Sheet Moulding Compounds (SMC);

coated substrates, such as powder-coated metals or alloys;

paints and varnishes, especially automobile finishes.

The substrates can be pretreated if necessary before the application of the epoxy resin composition. Such pretreatments include in particular physical and/or chemical cleaning methods, such as grinding, sand blasting, shot peening, brushing or the like, wherein the resulting dust is advantageously suctioned away, as well as further treatment with cleaning agents or solvents or the applying of an adhesion promoter, an adhesion promoting solution, or a primer.

The described epoxy resin composition is advantageously usable as a fiber composite, casting compound, sealant, adhesive, floor covering, coating, paint, varnish, seal, undercoat, primer, foam, block, elastomer, fiber, film or membrane.

In particular, it can be used as a casting compound, sealant and adhesive, for example, as an electrical casting compound, sealing compound, surfacer, joint sealant, mounting adhesive, chassis adhesive, sandwich element adhesive, half-shell adhesive, for example for rotor blades of wind power plants, bridge element adhesive, lamination adhesive, or anchoring adhesive, and also as a floor covering, coating, paint, varnish, seal, undercoat and primer for building and industrial applications, especially as a floor covering and floor coating for interior rooms such as offices, industrial bays, gymnasiums or cold storage rooms, or outdoors for balconies, patios, parking roofs, bridges or roofs, as a protective coating for concrete, cement, metals or plastics, for example, for surface sealing of loading areas, tanks, silos, shafts, pipelines, machinery or steel structures, such as those of ships, piers, offshore platforms, sluice gates, hydroelectric stations, waterways, swimming pools, wind power plants, bridges, chimneys, cranes or sheet piling, wherein these coatings protect the particular substrates especially against corrosion, abrasion, moisture, the effects of water and/or salt or chemicals, and also as an undercoat, primer, anticorrosion coat, or for making surfaces waterproof. The described composition is also especially suitable as a coating for so-called heavy corrosion protection in and at seawater. In particular, when the fully or partly hardened epoxy resin composition is being used as a coating, covering, or paint coat, it is possible to apply another coating, another covering or another paint coat to it, this additional layer also being an epoxy resin composition, or it can also be a different material, in particular, a polyurethane or polyurea coating.

The described epoxy resin composition is especially advantageously usable as a coating. By a coating is meant a layer of any kind that is applied in a sheet, especially paint coats, varnishes, sealants, undercoats and primers, as described above. The described epoxy resin composition is especially advantageously usable in low-emission systems with the Eco Seal of Approval, such as Emicode (EC1 Plus), AgBB, DIBt, Der Blaue Engel, AFSSET, RTS (M1) and US Green Building Council (LEED).

A further subject matter of the invention is thus the use of the described epoxy resin composition as a coating As a coating, the epoxy resin composition is used advantageously in a coating method wherein it has a fluid consistency with low viscosity and good spreading properties, and especially it can be applied as a self-spreading coating on predominantly level surfaces or as a paint coat. Preferably in this application the epoxy resin composition immediately after the mixing of the resin and the hardener component has a viscosity, measured at 20° C., in the range of 300 to 2000 mPa·s, preferably in the range of 300 to 1500 mPa·s, especially in the range of 300 to 1000 mPa·s. The blended composition is applied within the work time as a thin film with a layer thickness of typically around 50 μm to around 5 mm in a sheet on a substrate, typically at ambient temperature. The application is done, for example, by pouring out onto the substrate being coated. The composition in the liquid state is distributed uniformly with the help of a spatula or a trowel, for example. In addition, the composition once spread out can be leveled and freed of air bubbles with a spiked roller. But the application can also be done manually with a brush or roller, or as a spray application, for example, for an anticorrosion coating on steel. Upon hardening, there typically results largely clear, shiny and non-tacky films of little brittleness, having a good adhesion to the most diverse of substrates and possessing a high hardness. Thanks to the amine of formula (I) in the hardener, self-spreading epoxy resin coatings are possible which make do with little or no non-incorporable thinners, and whose content of primary amino groups can be kept so low in the coating that hardly any reactions with the $CO_2$ in the air occur. As a result, for the most part there are no blushing effects for the sheetlike application, even under unfavorable reaction conditions, that is, conditions which favor blushing, especially at low hardening temperatures in the range of 5 to 10° C. and high humidity.

A further subject matter of the invention is an article obtained by using the described epoxy resin composition as a coating.

The described epoxy resin composition is distinguished by numerous advantageous properties. It has only slight odor and is surprisingly fluid at room temperature, so that it can also be easily worked even without additional thinners, especially when applied in a sheet. It hardens at ambient temperature and surprisingly fast, especially also under damp and cold conditions, with no blushing effects, and in the hardened state it has a surprisingly high hardness with little brittleness. It is therefore able to easily withstand mechanical strain, which is especially important when used as a protective coating or as a floor covering. Hardened films are typically not cloudy and they have an evenly shiny, carter-free and non-tacky surface.

Epoxy resin compositions comprising at least one polyamine A in addition to the amine of formula (I) have especially advantageous properties. These epoxy resin compositions exhibit a surprising combination of benefits: on the one hand, the amine of formula (I) has an excellent thinning effect on the composition, so that the composition immediately after the blending of the components has a low viscosity, and on the other hand the composition hardens quickly. Furthermore, the amine of formula (I) lessens the tendency to blushing effects, and finally the composition hardens into films of outstanding quality in terms of clarity, shine, surface tackiness, high hardness and low brittleness. Due to the fact that the amine of formula (I) contains no primary amino groups and only two secondary amino groups, the quick hardening, the attainable high hardnesses and the non-tackiness are especially surprising.

EXAMPLES

Sample embodiments are presented below to explain more closely the described invention. Of course, the invention is not limited to these sample embodiments.

1. Description of the Measurement Methods

The amine content, that is, the total content of amino groups in the compounds produced, was determined by titration (with 0.1 N $HClO_4$ in glacial acetic acid, against crystal violet) and it is always indicated in mmol N/g.

Infrared spectra were measured as undiluted films on a Perkin-Elmer FT-IR 1600 instrument outfitted with horizontal ATR measurement unit with ZnSe crystal; the absorption bands are indicated in wave numbers ($cm^{-1}$) (measurement window: 4000-650 $cm^{-1}$).

$^1$H-NMR spectra were measured on a spectrometer type Bruker DPX-300 at 300.13 MHz; the chemical shifts δ are indicated in ppm relative to tetramethylsilane (TMS).

Mass spectra (FIMS) were measured on a high-resolution mass spectrometer of type Thermo Scientific LTQ Orbitrap XL, by injecting 500 μl of the sample dissolved in methanol (100 μg/ml) directly into the mass spectrometer at an injection rate of 10 μl/min. and a flow rate of the carrier (1 mM ammonium formate in methanol) of 500 μl/min; detection was done by means of electrospray ionization ($ESI^+$).

The viscosity (η) was measured at 20° C. on a thermostatically controlled cone and plate viscosimeter Rheotec RC30 (cone diameter 50 mm, cone angle 1°, distance from cone tip to plate 0.05 mm, shear rate 10-100 $s^{-1}$).

2. Substances Used

| | |
|---|---|
| EP-adduct 1: | reaction product of 116.0 wt. parts of 1,5-diamino-2-methyl-pentane and 182 wt. parts of Araldite ® DY-K; NH-Equivalent = 99.3 g/Eq; $\eta$ = 5830 mPa · s |
| EP-adduct 2: | reaction product of 136.2 wt. parts of 1,3-bis-(aminomethyl)benzene and 182 wt. parts of Araldite ® DY-K; NH-Equivalent = 106.1 g/Eq; $\eta$ = 59,490 mPa · s |
| Gaskamine ® A-229 (MGC) | reaction product of 1,3-bis-(aminomethyl)benzene with acrylonitrile; NH-Equivalent = 102 g/Eq; $\eta$ = 230 mPa · s |
| Gaskamine ® 240 (MGC) | styrolized 1,3-bis-(aminomethyl)benzene; NH-Equivalent = 103 g/Eq; $\eta$ = 165 mPa · s |
| Gaskamine ® 328 (MGC) | reaction product of 1,3-bis-(aminomethyl)benzene with epichlorhydrin; NH-Equivalent = 55 g/Eq; $\eta$ = 12,720 mPa · s |
| Polypox ® IH 7011 (UPPC Dow) | mod. polyamine, hardener for low-emission EP systems; NH-Equivalent = 82 g/Eq; $\eta$ = 810 mPa · s |
| Aradur ® 3442 (Huntsman) | phenalkamine; NH-Equivalent = 125 g/Eq; $\eta$ = 10,210 mPa · s |
| Araldite ® DY-K (Huntsman) | monoglycidyl ether of cresol; EEW around 182 g/Eq |
| Araldite ® GY 250 (Huntsman) | bisphenol-A-diglycidylether; Epoxy Equivalent around 187.5 g/Eq |
| Araldite ® DY-E (Huntsman) | monoglycidyl ether of a $C_{12}$- to $C_{14}$-alcohol; Epoxy Equivalent around 290 g/Eq |
| Ancamine ® K 54 (Air Products) | 2,4,6-tris-(dimethylaminomethyl)phenol |

3. Preparation of Amines

Amine 1: N,N'-dibenzyl-m-xylylene diamine

In a round-bottom flask, 21.2 g of benzaldehyde and 13.6 g of 1,3-bis-(aminomethyl)benzene was dissolved in sufficient isopropanol under a nitrogen atmosphere. The solution was stirred for 30 minutes at room temperature and then hydrogenated at a hydrogen pressure of 80 bar, a temperature of 80° C. and a flow rate of 3 ml/min on a continuously operating hydrogenation apparatus with Pd/C solid bed catalyst. For control of the reaction, IR spectroscopy was used to determine if the imine band at around 1665 cm$^{-1}$ had vanished. The solution was then concentrated down in a vacuum at 80° C. A clear, yellowish oil was obtained with a viscosity of 230 mPa·s at 20° C., an amine content of 6.41 mmol N/g and a purity of 94.4% (determined by gas chromatography).

FT-IR: 3024, 2910, 2810, 1604, 1494, 1452, 1108, 1028, 784, 732, 694.

$^1$H-NMR (CDCl$_3$, 300 K): $\delta$ 7.4-7.1 (m, 14H, Ar—H), 3.77 (s, 8H, CH$_2$), 1.70 (s, 2H, NH).

FIMS: m/z=317.20203 ([MH$^+$]; theoretical mass for C$_{22}$H$_{25}$N$_2$: 317.20123).

Amine 2: N-benzyl-3-(N-benzyl)aminomethyl-3,5,5-trimethylcyclohexylamine

In the same way as described for example 1, 21.2 g of benzaldehyde and 17.0 g of 1-amino-3-aminomethyl-3,5,5-trimethylcyclohexane (=isophorone diamine) were combined. A clear, colorless oil was obtained with a viscosity of 590 mPa·s at 20° C. and an amine content of 5.82 mmol N/g.

Amine 3: N,N-dibenzyl-2-methylpentane-1,5-diamine

In the same way as described for example 1, 21.2 g of benzaldehyde and 11.6 g of 1,5-diamino-2-methylpentane were combined. A clear, yellowish oil was obtained with a viscosity of 420 mPa·s at 20° C. and an amine content of 6.67 mmol N/g.

4. Preparation of Hardeners

Example 1 to 5

For each example, the hardener indicated in Table 1 from the prior art was blended with the amine 1 in the indicated amounts (in parts by weight) with the aid of a centrifugal mixer (SpeedMixer™ DAC 150, FlackTek Inc.). One hour after the blending, the viscosity of the resulting hardener was determined. (The ratio between the number of NH equivalents of amine 1 and the number of NH equivalents of the hardener of the prior art was each time 0.33.)

TABLE 1

Compositions and viscosities of the hardeners from examples 1 to 5, measured at 20° C.

| | Example | | | | |
|---|---|---|---|---|---|
| | 1 | 2 | 3 | 4 | 5 |
| EP-adduct 1 | 74.5 | — | — | — | — |
| EP-adduct 2 | — | 79.6 | — | — | — |
| Gaskamine ® 328 | — | — | 41.3 | — | — |
| Polypox ® IH 7011 | — | — | — | 61.5 | — |
| Aradur ® 3442 | — | — | — | — | 93.8 |
| Amine 1 | 39.6 | 39.6 | 39.6 | 39.6 | 39.6 |
| Viscosity without amine 1 [mPa · s] | 5830 | 59,490 | 12,720 | 810 | 10,210 |
| Viscosity with amine 1 [mPa · s] | 1710 | 5070 | 1600 | 420 | 1730 |

5. Preparation of Epoxy Resin Compositions

Examples and Comparison Examples 6 to 17

For each example, the ingredients indicated in tables 2 to 4 were blended in the indicated amounts (in parts by weight) with the aid of a centrifugal mixer (SpeedMixer™ DAC 150, FlackTek Inc.). Ten minutes after the blending, the viscosity of the compositions was determined each time ("viscosity (10')"). Furthermore, each time a first film was spread onto a glass plate in a layer thickness of 500 μm and kept at 23±1° C.

and 50±5% relative humidity (=standardized climate, hereinafter abbreviated as "NK"), or hardened. After 4 weeks, the aspect of the films was judged (indicated in the tables as "Aspect (NK)"). A film was judged "good" if it was clear and had a shiny and nontacky surface without structure. By "structure" is meant any kind of marking or pattern on the surface. Furthermore, the König hardness (pendulum hardness after König, measured per DIN EN ISO 1522) of the films was determined after 2 days ("König hardness (NK) (2 d)") and after 4 days ("König hardness (NK) (4 d)") and after 7 days ("König hardness (NK) (7 d)") and after 4 weeks ("König hardness (NK) (4 w)"). Furthermore, each time a second film was spread onto a glass plate in a layer thickness of 500 □m and this was kept immediately after the application for 7 days at 8° C. and 80% relative humidity and then for 4 weeks in the NK, or hardened. 24 hours after the application, a bottle cap of polypropylene was placed on the film, with a moist sponge placed underneath it. After another 24 hours, the sponge and the cap were removed and placed at a new site of the film, where it was again removed after 24 hours and put in a new place, for a total of 4 times. After this, the aspect of these films was judged (indicated in the tables as "Aspect (8°/80%)"), in the same way as described for the Aspect (NK). Each time, the number of marks that were visible in the film due to the moist sponge and/or the cap was also indicated. If a discoloration or cloudiness occurred at the mark, this is likewise indicated. Once again, the König hardness was determined for these hardened films, each time after 7 days at 8° C. and 80% relative humidity ("König h. (8°/80%) (7 d cold)"), then after another 2 days in the NK ("König h. (8°/80%) (+2 d NK)") and 7 days in the NK ("König h. (8°/80%) (+7 d NK)") and 4 weeks in the NK ("König h. (8°/80%) (+4 w NK)"). On the first films hardened in the standardized climate, the tendency to splintering was determined after 2 months as a measure of the brittleness (indicated in the tables as "Splinter Tendency"), by peeling shavings from the film using an awl pressed at a slant with an angle of around 45°. If this occurred with no film fragments being splintered off, the splinter tendency was judged as "none". Otherwise, it was judged as "weak", "medium", or "strong", depending on how easily fragments are splintered from the film under the pressure of the blade tip to lift off a shaving. The results are indicated in tables 2 to 4.

TABLE 2

Composition and properties of example 6 and comparison examples 7 to 10.

| | | | example | | | |
|---|---|---|---|---|---|---|
| | | 6 | 7 (comp.) | 8 (comp.) | 9 (comp.) | 10 (comp.) |
| Araldite ® GY-250 | | 167.2 | 167.2 | 167.2 | 167.2 | 167.2 |
| Araldite ® DY-E | | 31.8 | 31.8 | 31.8 | 31.8 | 31.8 |
| Amine 1 | | 158.2 | — | — | — | — |
| Amine 2 | | — | 175.3 | — | — | — |
| Amine 3 | | — | — | 148.2 | — | — |
| Gaskamine ® A-229 | | — | — | — | 102.0 | — |
| Gaskamine ® 240 | | — | — | — | — | 103.0 |
| Ancamine ® K 54 | | 7.1 | 7.5 | 6.9 | 6.0 | 6.0 |
| Viscosity (10') [Pa · s] | | 0.34 | 0.95 | 0.33 | 0.62 | 0.68 |
| König hardness [s] | | | | | | |
| (NK) | (2 d) | 27 | n.m. | 10 | n.m. | 127 |
| | (4 d) | 108 | n.m. | 27 | 43 | 167 |
| | (7 d) | 146 | 62 | 34 | 76 | 179 |
| | (4 w) | 154 | 130 | 36 | 97 | 195 |
| Aspect (NK) | | good | good | good | good | good |
| König h · [s] | (7 d cold) | 6 | 4 | 10 | n.m. | 83 |
| (8°/80%) | (+2 d NK) | 78 | 22 | 27 | 25 | n.b. |
| | (+7 d NK) | 161 | 126 | 52 | 99 | 169 |
| | (+4 w NK) | 169 | 150 | 53 | 127 | 174 |
| Aspect (8°/80%) | | good | good | good | good | good |
| Number of marks | | 3 | 4 | 4 | 4 | 1 |

"n.m." stands for "not measurable", since the film was sticky;

"König h." stands for "König hardness";

TABLE 3

Composition and properties of example 12 and comparison examples 11 and 13 to 16.

| | | example | | | | | |
|---|---|---|---|---|---|---|---|
| | | 11 (comp.) | 12 | 13 (comp.) | 14 (comp.) | 15 (comp.) | 16 (comp.) |
| Araldite ® GY-250 | | 167.2 | 167.2 | 167.2 | 167.2 | 167.2 | 167.2 |
| Araldite ® DY-E | | 31.8 | 31.8 | 31.8 | 31.8 | 31.8 | 31.8 |
| EP-adduct 1 | | 99.3 | — | 74.5 | 74.5 | 74.5 | 74.5 |
| Hardener from example 1 | | — | 114.1 | — | — | — | — |
| Gaskamine ® A-229 | | — | — | 25.5 | — | — | — |
| Gaskamine ® 240 | | — | — | — | 25.8 | — | — |
| Amine 2 | | — | — | — | — | 43.8 | — |
| Amine 3 | | — | — | — | — | — | 37.1 |
| Ancamine ® K 54 | | 6.0 | 6.3 | 6.0 | 6.0 | 6.4 | 6.4 |
| Viscosity (10') [Pa · s] | | 1.90 | 0.85 | 0.80 | 0.82 | 0.97 | 1.08 |
| König hardness [s] | | | | | | | |
| (NK) | (2 d) | 181 | 129 | 60 | 80 | 77 | 116 |
| | (4 d) | 189 | 171 | 97 | 127 | 123 | 160 |
| | (7 d) | 200 | 182 | 112 | 147 | 148 | 176 |
| | (4 w) | 193 | 199 | 130 | 167 | 164 | 193 |
| Aspect (NK) | | good | good | good | good | good | good |
| König h. [s] | (7 d cold) | 101 | 70 | 39 | 52 | 39 | 42 |

TABLE 3-continued

Composition and properties of example 12 and comparison examples 11 and 13 to 16.

| | | example | | | | | |
|---|---|---|---|---|---|---|---|
| | | 11 (comp.) | 12 | 13 (comp.) | 14 (comp.) | 15 (comp.) | 16 (comp.) |
| (8°/80%) | (+2 d NK) | 174 | 119 | 81 | 94 | 90 | 66 |
| | (+7 d NK) | 192 | 160 | 115 | 119 | 147 | 133 |
| | (+4 w NK) | 197 | 186 | 125 | 147 | 174 | 186 |
| Aspect (8°/80%) | | sl. dull | good | good | sl. sticky | good | good |
| Number of marks | | 4 weak | 4 v. weak. | 4 weak | 4 weak | 4 weak | 4 v. weak |
| Splinter tendency | | medium | weak | weak | medium | weak | weak |

"sl." stands for "slightly";
"v. weak" stands for "very weak";
"König h." stands for "König hardness";
"comp." stands for "comparison"

TABLE 4

Composition and properties of example 18, 20 and 22 and comparison examples 17, 19 and 21.

| | | example | | | | | |
|---|---|---|---|---|---|---|---|
| | | 17 (comp.) | 18 | 19 (comp.) | 20 | 21 (comp.) | 22 |
| Araldite ® GY-250 | | 167.2 | 167.2 | 167.2 | 167.2 | 167.2 | 167.2 |
| Araldite ® DY-E | | 31.8 | 31.8 | 31.8 | 31.8 | 31.8 | 31.8 |
| EP-adduct 2 (MXDA) | | 106.1 | — | — | — | — | — |
| Hardener from example 2 | | — | 119.2 | — | — | — | — |
| Polypox ® IH 7011 | | — | — | 82.0 | — | — | — |
| Hardener from example 4 | | — | — | — | 101.1 | — | — |
| Aradur ® 3442 | | — | — | — | — | 125.0 | — |
| Hardener from example 5 | | — | — | — | — | — | 133.4 |
| Ancamine ® K 54 | | 6.1 | 6.4 | 5.6 | 6.0 | 6.5 | 6.6 |
| Viscosity (10') [Pa · s] | | 6.96 | 2.39 | 0.93 | 0.66 | 2.82 | 1.03 |
| König hardness [s] | | | | | | | |
| (NK) | (2 d) | 218 | 195 | 118 | 122 | 52 | 71 |
| | (4 d) | 223 | 206 | 108 | 146 | 120 | 112 |
| | (7 d) | 232 | 216 | 150 | 192 | 134 | 132 |
| | (4 w) | 231 | 213 | 153 | 211 | 151 | 165 |
| Aspect (NK) | | good | good | good | good | good | good |
| König h. [s] | (7 d cold) | 139 | 98 | 46 | 53 | 70 | 49 |
| (8°/80%) | (+2 d NK) | 207 | 161 | 89 | 110 | 78 | 64 |
| | (+7 d NK) | 217 | 185 | 141 | 174 | 81 | 123 |
| | (+4 w NK) | 216 | 206 | 141 | 191 | 123 | 144 |
| Aspect (8°/80%) | | dull | dull | good | good | good | good |
| Number of marks | | 4 white | 4 weak | 1 | 1 | 1 weak | 1 v. weak. |
| Splinter tendency | | medium | weak | none | none | strong | weak |

"white" stands for a white discoloration of the marks,
"v. weak" stands for "very weak";
"König h." stands for "König hardness";
"comp." stands for "comparison"

The invention claimed is:

1. Epoxy resin composition comprising:

a) at least one epoxy resin, and b) at least one hardener, suitable for the hardening of epoxy resins, comprising an amine of formula (I):

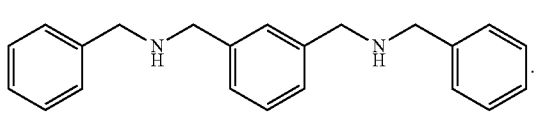

(I)

2. Epoxy resin composition according to claim 1, wherein the hardener furthermore comprises at least one polyamine, which has at least three amine hydrogens reactive to epoxy groups.

3. Epoxy resin composition according to claim 2, wherein the polyamine is selected from the group consisting of 1,3-pentane diamine, 1,5-diamino-2-methylpentane, 2-butyl-2-ethyl-1,5-pentane diamine, 1,6-hexane diamine, 2,2,4- and 2,4,4-trimethylhexamethylene diamine, 1,12-dodecane diamine, 1,3-diaminocyclohexane, bis-(4-aminocyclohexyl)methane, bis-(4-amino-3-methylcyclohexyl)methane, 1-amino-3-aminomethyl-3,5,5-trimethylcyclohexane, 1,3-bis-(aminomethyl)cyclohexane, 1,3-bis-(aminomethyl)benzene, bis-hexamethylene triamine, diethylene triamine, triethylene tetramine, tetraethylene pentamine, pentaethylene hexamine polyethylene polyamines with 5 to 7 ethylene amine units, dipropylene triamine, N-(2-aminoethyl)-1,3-propane diamine, N,N'-bis(3-aminopropyl)ethylene diamine, polyoxyalkylene diamines and polyoxyalkylene triamines with a molecular weight in the range of 200 to 500 g/mol, polyamidoamines, phenalkamines, compounds of the mentioned polyamines fully or partly alkylated to primary amino groups and adducts of the mentioned polyamines with epoxides and epoxy resins.

4. Epoxy resin composition according to claim 2, wherein the polyamine has at least one secondary amino group.

5. Epoxy resin composition according to claim 2, wherein a ratio of the number of amine hydrogens of the amine of formula (I) that are reactive to epoxy groups and the number of amine hydrogens of the polyamine that are reactive to epoxy groups lies in a range of 0.05:1 to 5:1.

6. Epoxy resin composition according to claim 2, wherein a weight ratio of the amine of formula (I) and the polyamine lies in a range of 0.2:1 to 2:1.

7. Epoxy resin composition according to claim 2 further comprising non-reactive thinners in the hardener, wherein when present, the content of non-reactive thinners is less than 25 wt. %.

8. Epoxy resin composition according to claim 1, wherein the epoxy resin is a liquid resin based on a bisphenol.

9. Epoxy resin composition according to claim 1, wherein the epoxy resin composition furthermore contains at least one reactive thinner having at least one epoxy group.

10. Epoxy resin composition according to claim 1, wherein the epoxy resin composition is a two-component composition consisting of
(i) a resin component containing the at least one epoxy resin and
(ii) a hardener component containing the hardener.

11. Hardened composition obtained from the hardening of a composition according to claim 1.

12. A method for coating a substrate, comprising coating the substrate with the epoxy resin composition according to claim 1.

13. Article obtained by the method according to claim 12.

14. A hardener suitable for the hardening of epoxy resins, comprising an amine of formula (I)

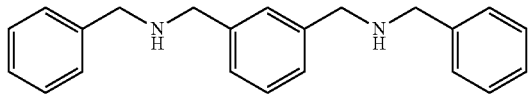
(I)

and at least one polyamine, which has at least three amine hydrogens reactive to epoxy groups.

15. The hardener suitable for the hardening of epoxy resins according to claim 14, wherein the polyamine is selected from the group consisting of 1,3-pentane diamine, 1,5-diamino-2-methylpentane, 2-butyl-2-ethyl-1,5-pentane diamine, 1,6-hexane diamine, 2,2,4- and 2,4,4-trimethylhexamethylene diamine, 1,12-dodecane diamine, 1,3-diaminocyclohexane, bis-(4-aminocyclohexyl)methane, bis-(4-amino-3-methylcyclohexyl)methane, 1-amino-3-aminomethyl-3,5,5-trimethylcyclohexane, 1,3-bis-(aminomethyl)cyclohexane, 1,3-bis-(aminomethyl)benzene, bis-hexamethylene triamine, diethylene triamine, triethylene tetramine, tetraethylene pentamine, pentaethylene hexamine polyethylene polyamines with 5 to 7 ethylene amine units, dipropylene triamine, N-(2-aminoethyl)-1,3-propane diamine, N,N'-bis(3-aminopropyl)ethylene diamine, polyoxyalkylene diamines and polyoxyalkylene triamines with a molecular weight in the range of 200 to 500 g/mol, polyamidoamines, phenalkamines, compounds of the mentioned polyamines fully or partly alkylated to primary amino groups and adducts of the mentioned polyamines with epoxides and epoxy resins.

16. A method of hardening an epoxy resin, comprising mixing an epoxy resin with a hardener at ambient temperature comprising an amine of formula (I)

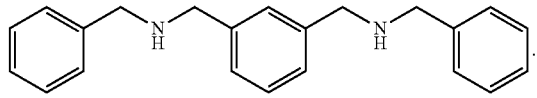
(I)

17. The method of hardening an epoxy resin according to claim 16, wherein the hardener further comprises at least one polyamine, which has at last three amine hydrogens reactive to epoxy groups of the epoxy resin.

* * * * *